United States Patent [19]
Jakob et al.

[11] Patent Number: 5,474,892
[45] Date of Patent: Dec. 12, 1995

[54] METHOD FOR THE STABILIZATION OF PROTEINS USING HEAT SHOCK PROTEIN HSP90

[76] Inventors: Ursula Jakob, Franz-von-Taxis-Ring 58; Johannes Buchner, Arndstrasse 11, both of 8400 Regensburg; Hans Wiech, Stautenbergring 1; Richard Zimmermann, Herzberger Landstrasse 110, both of 3400 Göttingen; Rainer Rudolph, Färbergasse 17, 8120 Weilheim, all of Germany

[21] Appl. No.: 5,706

[22] Filed: Jan. 19, 1993

[30] Foreign Application Priority Data

Jan. 17, 1992 [DE] Germany .................... 42 01 181.7

[51] Int. Cl.$^6$ ................ C12Q 1/00; G01N 1/00
[52] U.S. Cl. ................ 435/4; 436/8; 436/176; 435/963
[58] Field of Search ............ 530/350; 435/69.1, 435/4, 963; 436/176, 8

[56] References Cited

U.S. PATENT DOCUMENTS 5,302,518  4/1994  Neupert et al. ............ 435/69.1

OTHER PUBLICATIONS

Onate et al, Md. Endocrin. 5(12):1993–2004, 1991.
Giovanella, Adv. Exp. Med. Biol 267:95–98, 1990.
Nagao et al, Adv. Genet. 28:235–74, 1990.
Hubbard et al, Prot. Eng. 4(2):711–717, 1991.
Hardesty et al, Biochem Cell Biol 67(11–12):749–750, 1989.
Schlesinger, J. Biol Chem. 265(21):12111–12114, 1990.
Badcoe et al, Biochem. 30(38):9195–9200, 1991.
Miyuta et al, J. Biol Chem 267(10):7042–7047, 1992.
Lindquist et al, Annual Rev. Genetics 22:631–77, 1988.
Pelham, Cell 46:954–961, 1986.
Buchner et al, Biochem. 30:1586–1591, 1991.
Ellis, Nature 328:378–379, 1987.
Jacttela et al, Ann. Med. 24(4):249–258, 1992.
Lorimer et al, Philos. Trns. R. Soc. Lond, Biol. 339:297–303, 1993.
Wiech, H., et al. Nature, 358:169–170 (1992).
Gething, M–J, et al. Nature, 355:33–45 (1992).
Ellis, R. J., Annu. Rev. Biochem. 60:321–47 (1991).

*Primary Examiner*—Christine M. Nucker
*Assistant Examiner*—Julie Krsek-Staples

[57] ABSTRACT

The present invention concerns a method for the stabilization of proteins in an aqueous solution which is characterized in that one or several members of the heat shock protein (Hsp90) family are added to the aqueous solution containing protein.

10 Claims, 2 Drawing Sheets

METHOD FOR THE STABILIZATION OF PROTEINS USING HEAT SHOCK PROTEIN HSP90

The present invention concerns a method for the stabilization of proteins in an aqueous solution by addition of a protein component acting as a stabilizer.

Proteins of the Hsp (heat shock protein) 90 family, which in their active form are generally present as dimers, are known in prokaryotic as well as in eukaryotic organisms. The Hsp90-homologous protein isolated from *E. coli* is denoted Htp G (Bardwell & Graig, Proc. Natl. Acad. Sci. USA 84 (1987), 5177–5181). Furthermore a Hsp90 gene product is for example known in Drosophila melanogaster (Blackman and Meselson, J. Mol. Biol. 188 (1986), 499–515), while several Hsp90 gene products are known in humans (Simon et al., Mol. Cell. Biol. 7 (1987), 2884–2890; Sorger et al., Nature 329 (1987), 81–84).

Strong homologies have been found when sequences of proteins of the Hsp90 family from different organisms are compared. The proteins of the eukaryotic organisms which are furthest apart on the evolutionary scale still share about 50% homologies at the amino acid level. The homologies between the respective proteins from eukaryotes and prokaryotes are about 40% (Bardwell and Craig, Proc. Natl. Acad. Aci. U.S.A. 84 (1987), 5177–5181).

All eukaryotic members of the Hsp90 family known up to now have a region which is strongly negatively charged at a similar position in the N-terminus whose amino acid sequence is only slightly conserved. A further region which is strongly negatively charged is located at the C-terminus in eukaryotic as well as in prokaryotic Hsp90 molecules which is also not conserved apart from the last four amino acids. This sequence Glu-Glu-Val-Asp has so far been found in all the known members of the Hsp90 family.

Regarding the function of Hsp90, it is so far known that it interacts in vivo with different tyrosine kinases, e.g. with retroviral kinases (Brugge et al., Cell 25 (1981), 363–372; Lindquist and Craig, Ann. Rev. Genet 22 (1988), 631–677) as well as with the haem-regulated cellular eIF2α kinase (Rose et al., Biochemistry 26 (1987), 6583–6587) and can influence their degree of phosphorylation and activity.

In addition it is known that members of the Hsp90 family can bind to steroid hormone-receptor complexes (Pratt et al., J. Biol. Chem. 263 (1988), 267–273; Welch (1990), in "Stress Proteins in Biology and Medicine", edited by: Morimoto, R. I., Tissiéres, A. & Georgopoulos, C., Cold Spring Harbor Laboratory Press, Cold Spring Harbor, New York, p. 223–278).

Hsp90 can also bind to actin and form cross-linkages between actin filaments (Koyasu et al., Proc. Natl. Acad. Sci. U.S.A. 83 (1986), 8054–8058). Finally it is also known that Hsp90 can cause the dissociation of a hormone-free glucocorticoid receptor from a DNA receptor complex (Scherer et al., J. Biol. Chem. 265 (1990), 21397–21400).

Stabilization of proteins by addition of different protein components acting as stabilizers is known. The disadvantages of known stabilizer proteins are, however, that they are only effective in the presence of ATP, they have to be used in a large molecular excess or/and are themselves complicated oligomers composed of more than 10 subunits.

Thus the object of the present invention is to provide a new method for the stabilization of proteins in an aqueous solution in which the disadvantages mentioned above are at least partially eliminated.

The object according to the present invention is achieved by providing a method for stabilizing proteins in an aqueous solution which is characterized in that one or several members of the "Hsp90" protein family are added to the aqueous solution containing protein.

It was surprisingly found that "Hsp90" proteins can stabilize other proteins in an aqueous solution whereby this stabilizing effect is in particular based on the prevention of the formation of insoluble aggregates. The method according to the present invention can for example be used to facilitate the in vitro folding of native proteins in a dissolved form.

The method according to the present invention can be used for any proteins. It is preferably used for those proteins which tend to readily aggregate in a dissolved form because of their temperature sensitivity or for other reasons. An important field of application for the method according to the present invention is the stabilization of solutions which contain the enzymatically active proteins (e.g. citrate synthase).

A further important field of application is the stabilization of solutions containing antibodies or derivatives derived from antibodies (e.g. Fab or F(ab)$_2$ fragments).

Although the "Hsp90" proteins cause a stabilization of proteins at any protein concentrations, a particularly good stabilization effect is achieved in a concentration range of 0.0001 μmol/l to 100 μmol/l of the protein to be stabilized.

The molar ratio between the protein to be stabilized and the "Hsp90" protein added in the method according to the present invention is preferably 0.0001:1 to 10:1. In this case this molar ratio refers to the Hsp90 complex which generally has two subunits. The "Hsp90" protein is particularly preferably added at a molar ratio of 0.001:1 to 5:1 in relation to the proteins to be stabilized.

A particular advantage of the method according to the present invention is that the proteins can be stabilized in the absence of ATP or that an addition of ATP generally has no influence on the stabilizing effect of the "Hsp90" protein. In this way it is easily possible to stabilize protein solutions for enzymatic tests in which ATP is used as the cosubstrate without this having an interfering influence on the enzymatic test.

The stabilization of proteins according to the present invention is observed with "Hsp90" proteins which can be derived from prokaryotic or eukaryotic organisms. The purification of the "Hsp90" protein from bovine pancreas is for example carried out according to the method described by Welch and Feramisco (J. Biol. Chem. 257, (1982) 14949–14959). A list of further "Hsp90" proteins which are homologous to this protein and which can be used in the method according to the present invention may be found in Lindquist, S. C. and Craig, E. A. (1988), Ann. Rev. Genet. 22: 631–677.

A preferred application of the method according to the present invention is to facilitate in vitro folding or renaturation of denatured proteins. In this case these are preferably proteins which have been synthesized by heterologous expression in prokaryotes and which usually accumulate in this process in the form of inclusion bodies. The heterologously expressed proteins are preferably eukaryotic proteins. The term "heterologous expression" in this connection means that a protein is isolated from a foreign (heterologous) organism or/and is expressed in a cell, particularly a prokaryotic cell, under the control of a foreign (heterologous) promoter and is subsequently isolated from the cell or the culture medium. This heterologous expression of proteins is a standard method which is known to a person skilled in the area of molecular biology and does not need to be elucidated in detail here. In this connection reference is for example made to the description of the expression of cloned genes by Sambrook et al., (Molecular Cloning. A Laboratory Manual, Cold Spring Harbor Laboratory Press (1989), chapters 16 and 17).

A further preferred field of application of the method according to the present invention is the stabilization of native proteins in a dissolved form. Thus it is for example possible by adding "Hsp90" proteins to maintain a constant sensitivity of optical tests in solutions containing protein in which interferences can be caused by a low stability of protein components present in the test solution. Such an optical test for example preferably comprises an enzymatic reaction, particularly preferably an enzymatic reaction in which ATP is present as a cosubstrate.

An "optical test" within the sense of the present invention is a method of determination in which an optical parameter or the change in an optical parameter, e.g. absorbance, transmission, scattered light etc., is measured. The present invention is preferably used in methods in which scattered light is determined e.g. in turbidometric, nephelometric or fluorimetric methods.

In addition solutions containing proteins can be stabilized which contain antibodies or derivatives derived from antibodies.

The present invention in addition also concerns a reagent for stabilizing proteins in an aqueous solution; this reagent can be in a solid or liquid form and contains one or several "Hsp90" proteins, in particular the "Hsp90" protein from bovine pancreas. A reagent according to the present invention can for example contain the "Hsp90" protein in a dissolved form or/and as a lyophilisate.

It is intended to elucidate the invention further by the following examples in conjunction with the figures.

EXAMPLES

Materials: Citrate synthase from pig heart (Boehringer Mannheim GmbH, Order No. 103 373).

The purification of "Hsp90" from bovine pancreas is carried out according to Welch and Feramisco (1982), J. Biol. Chem. 257, 14949–14959.

220 g bovine pancreas were cut up mechanically and homogenized. After lysing the cells, the homogenate was differentially centrifuged at 140000×g in a sucrose gradient and the cytosolic supernatant was separated on a DE52 anion exchange chromatography column. The Hsp90 eluate (200–240 mmol/l NaCl) was chromatographed again on the DE52-column. Hsp90 was eluted between 175 mmol/l and 250 mmol/l NaCl. This was followed by anion exchange chromatography with hydroxylapatite and gel filtration with Superose 6.

The Fab fragment and the complete MAB33 antibody of the IgG1 class from the mouse are described in the following publications:

1) Buckel, P., Hübner-Parajsz, C., Mattes, R., Lenz, H., Haug, H. & Beaucamp, K., (1987), Gene 51: 13–19
2) EP-A 0 364 926.

Example 1

Influence of "Hsp90" on the aggregation of renatured citrate synthase.

Denaturation of citrate synthase was carried out by incubation of 15 µmol/l citrate synthase in 6.0 mol/l guanidinium.HCl (Gdn.HCl), 20 mmol/l DTE, 50 mmol/l Tri/HCl, 2 mmol/l EDTA, pH 8 for 2 hours at 20° C.

Subsequently the citrate synthase was renatured in the absence or presence of "Hsp90". For this denatured citrate synthase (see above) was dissolved while stirring in a ratio of 1:100 in Lo buffer (40 mmol/l 4-(2-hydroxy-ethyl)-1-piperazine-ethane sulfonic acid (HEPES), 20 mmol/l KOH, 20 mmol/l KCl, 10 mmol/l $(N_4)_2SO_4$, 2 mmol/l potassium acetate, 0.5 mmol/l EDTA, 1 mmol/l dithiothreitol (DTT), pH 7.0) containing different concentrations of "Hsp90". The aggregation of citrate synthase (final concentration 0.15 µmol/l) was determined by measuring the light scattering at an emission and excitation wavelength of 500 nm for the first 5 minutes. The dead time was about 5 seconds. The aggregation is stated in random units. The total volume of the reaction mixture was 1500 µl. Four reaction mixtures were prepared altogether:

1. Lo buffer
2. Lo buffer, 0.16 µmol/l Hsp90
3. Lo buffer, 0.27 µmol/l Hsp90
4. Lo buffer, 0.54 µmol/l Hsp90

Figure 1:
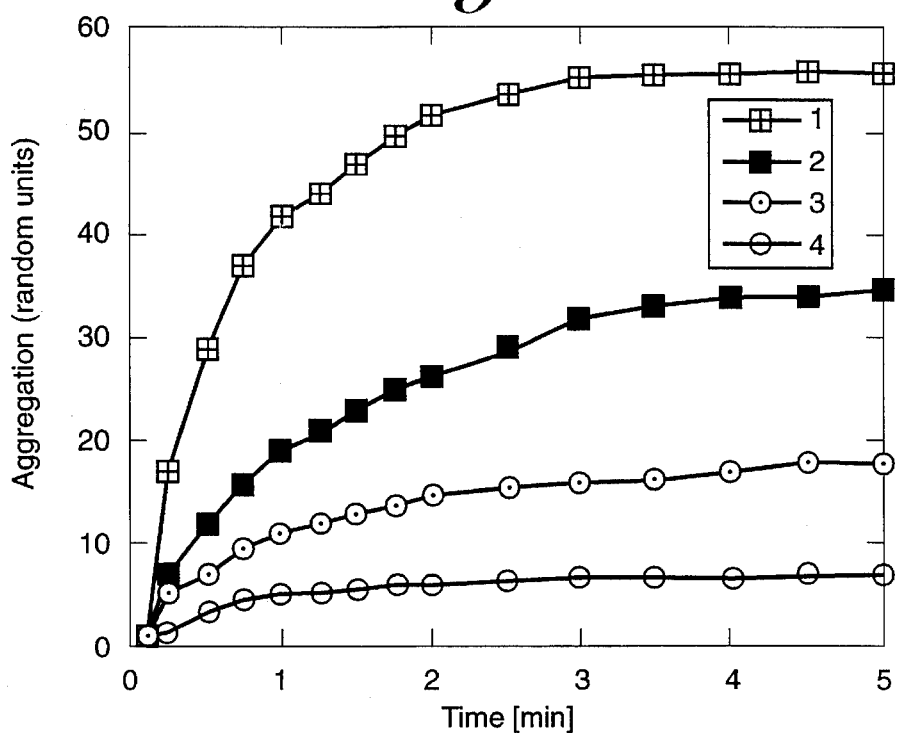
FIG. 1 shows an aggregation timecourse for the renaturation of citrate synthase in relation to the "Hsp90" concentration.

It can be seen from FIG. 1 that a large decrease in the aggregation was observed with increasing concentrations of "Hsp90".

Example 2

Influence of "Hsp90" on the reactivation of citrate synthase.

The denaturation of citrate synthase was carried out as described in example 1.

The reactivation kinetics of denatured citrate synthase was determined as follows:

Denatured citrate synthase was diluted 1:100 in the reactivation mixture while stirring (final concentration 0.15 µmol/l) and incubated at 20° C. Aliquots are taken from the reaction mixture at defined times and used to determine the activity in the citrate synthase activity test. The activity of native citrate synthase after a two hour incubation at 20° C. is set as 100%. The total volume of the reactivation mixtures was 300 µl.

The citrate synthase activity test was carried out as follows:

Citrate synthase catalyses the synthesis of citrate from oxaloacetate and acetyl-CoA. In this process SH-CoA is released and the SH group which forms is detected with the aid of the Ellman reagent, DTNB (5,5'-dithio-bis-2-nitrobenzoic acid) by the release of the yellow 2-mercapto-5-nitrobenzoic acid.

| Contained in the test mixture: | Concentration of the stock solution | Concentration in the test |
| --- | --- | --- |
| 10 µl | oxaloacetate (1.37 mg/ml) | 0.10 mmol/l |
| 30 µl | acetyl-CoA (4.1 mg/ml) | 0.15 mmol/l |
| 10 µl | DTNB (3.96 mg/ml) | 0.10 mmol/l |
| 20 µl | citrate synthase | |
| 930 µl | 50 mmol/l Tris/HCl, 2 mmol/l EDTA, pH 8.0 | |

The specific activity of citrate synthase can be calculated from the increase in absorbance at 412 nm in relation to time.

The following mixtures were prepared:

1. Lo buffer, 1 mg/ml bovine serum albumin (BSA)
2. Lo buffer, 1 mg/ml BSA, 0.15 µmol/l Hsp90
3. Lo buffer, 1 mg/ml BSA, 0.15 µmol/l heat denatured Hsp90 (incubation 15 minutes, 95° C).

Figure 2:
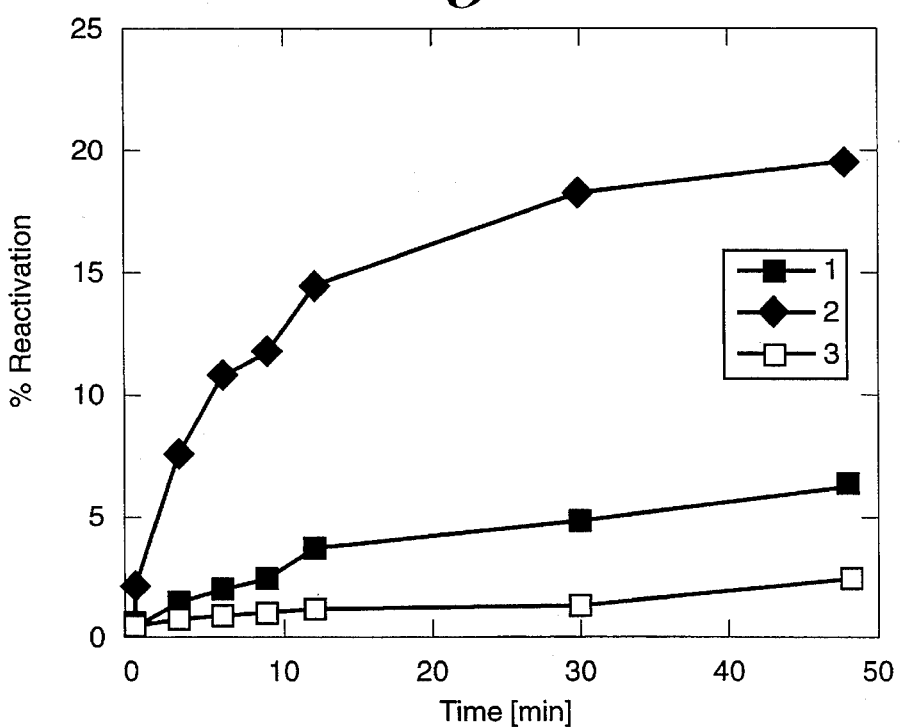
FIG. 2 shows the reactivation kinetics of denatured citrate synthase at 20° C. in the presence or absence of active "Hsp90

FIG. 2 shows that a significant increase in the activity of citrate synthase was only observed in the presence of active Hsp90.

Example 3

Influence of Hsp90 on the reactivation and stabilization of citrate synthase at 37° C.

The determination of the reactivation kinetics was carried out as described in example 2 with the exception that the denatured citrate synthase was added to the reactivation mixture at 37° C.

The following mixtures were prepared:

1. Lo buffer
2. Lo buffer, 0.075 µmol/l Hsp90
3. Lo buffer, 0.15 µmol/l Hsp90

Figure 3:
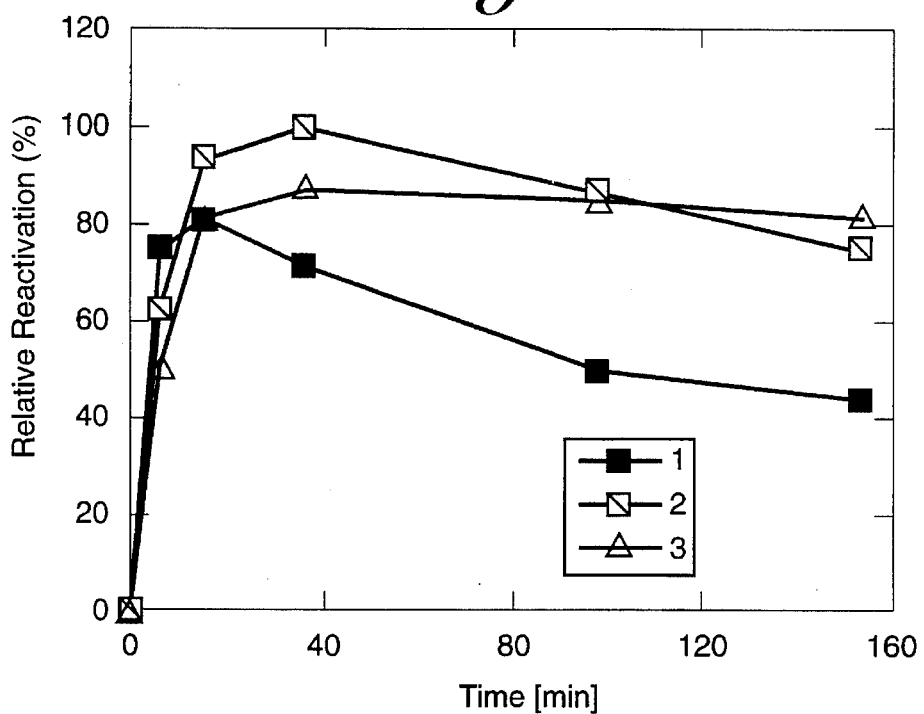
" and FIG. 3 shows the reactivation kinetics of denatured citrate synthase at 37° C. in the presence or absence of active "Hsp90

FIG. 3 shows that the citrate synthase is a thermally unstable protein. Even at 37° C. the enzyme tends to aggregate under the selected buffer conditions. Stabilization by active Hsp90 is apparent in FIG. 3 (cf. 1 and 3): in the absence of active Hsp90 the reactivation yield of denatured citrate synthase already decreases about 20 minutes after the start of the renaturation due to thermal inactivation of the refolded citrate synthase. In the presence of Hsp90 the reactivation yield of the citrate synthase increases and the inactivation of the renatured citrate synthase is increasingly reduced in relation to the Hsp90 concentration. This is proven by the finding that in addition to an improvement in renaturation the citrate synthase molecules which have already been activated are stabilized by Hsp90.

Example 4

Influence of "Hsp90" on the reactivation of denatured Fab fragments

Denaturation of the Fab fragments

Denaturation of Fab was carried out by incubation of 0.1.5 µmol/l Fab in 6.0 mol/l Gdn.HCl, 50 mmol/l Tris/HCl, 2 mmol/l EDTA, pH 8.0 for 2 hours at 20° C. Subsequently renaturation of the Fab fragments was carried out in the absence or presence of "Hsp90". For this, denatured Fab was diluted in the reactivation mixture at a ratio of 1:100 while stirring (final concentration 0.15 µmol/l) and incubated at 20° C.

Aliquots were taken from the reaction mixture at defined times and the reaction was demonstrably stopped by diluting the aliquots in buffer E (50 mmol/l Tris/HCl, 50 mmol/l NaCl, TX-100, pH 8.0)+trypsin (30 µg/ml) at a ratio of 1:50 and storing on ice.

An ELISA (enzyme-linked immunosorbent assay) was carried out in order to determine the reactivation yield of Fab (Buchner, J. & Rudolph, R. (1991), BioTechnology 9: 157–162).

Reaction mixtures:

1. 50 mmol/l Tris/HCl, 2 mmol/l EDTA, pH 8.0
2. 50 mmol/l Tris/HCl, 2 mmol/l EDTA, pH 8.0, 0.075 µmol/l Hsp90
3. 50 mmol/l Tris/HCl, 2 mmol/l EDTA, pH 8.0 0.075 µmol/l heat denatured Hsp90 (incubation for 30 minutes, 95° C.)

Figure 4:
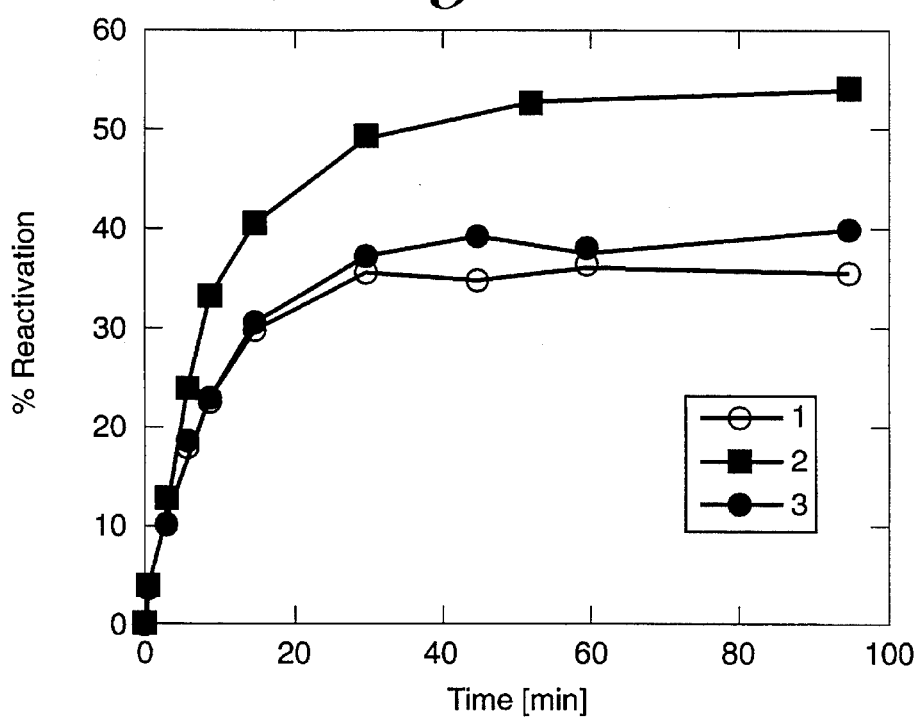
" and FIG. 4 shows the reactivation kinetics of denatured Fab fragments (MAB33 from the mouse) in the presence or absence of active "Hsp90".

It can be seen from FIG. 4 that the reactivation yield significantly increases in the presence of active "Hsp90".

We claim:

1. A method for stabilizing a protein in an aqueous solution comprising adding a Hsp90 protein to said aqueous solution.

2. A method for stabilizing a protein in an aqueous solution according to claim 1, wherein said aqueous solution contains an enzymatically active protein in need of stabilization.

3. A method for stabilizing a protein in an aqueous solution according to claim 1, wherein said aqueous solution contains an antibody or an antibody derivative in need of stabilization.

4. A method for stabilizing a protein in an aqueous solution according to claim 1, wherein said Hsp90 protein is derived from a prokaryote.

5. A method for stabilizing a protein in an aqueous solution according to claim 1, wherein said Hsp90 protein is derived from a eukaryote.

6. A method for stabilizing a protein in an aqueous solution according to claim 1, wherein said Hsp90 protein is derived from bovine pancreas.

7. A stabilized reagent comprising:

(i) at least one protein and
(ii) an amount of a purified and isolated Hsp90 protein sufficient to stabilize said protein.

8. A stabilized reagent according to claim 7, in the form of a solution.

9. A stabilized reagent according to claim 7, in the form of a lyophilisate.

10. A stabilized reagent according to claim 7, wherein said Hsp90 protein is derived from bovine pancreas.

* * * * *

UNITED STATES PATENT AND TRADEMARK OFFICE
CERTIFICATE OF CORRECTION

PATENT NO. : 5,474,892
DATED : December 12, 1995
INVENTOR(S) : Ursula Jakob, et al.

It is certified that error appears in the above-indentified patent and that said Letters Patent is hereby corrected as shown below:

On the title page, please insert the Assignee as follows:
-- Boehringer Mannheim GmbH, Mannheim Germany --.

Signed and Sealed this

Twenty-first Day of May, 1996

Attest:

BRUCE LEHMAN

Attesting Officer     Commissioner of Patents and Trademarks